US009757160B2

(12) United States Patent
Gordon

(10) Patent No.: US 9,757,160 B2
(45) Date of Patent: Sep. 12, 2017

(54) DEVICE AND METHOD FOR TREATMENT OF SPINAL DEFORMITY

(71) Applicant: Globus Medical, Inc, Audubon, PA (US)

(72) Inventor: Jeffrey David Gordon, Newtown Square, PA (US)

(73) Assignee: Globus Medical, Inc., Audubon, PA (US)

( * ) Notice: Subject to any disclaimer, the term of this patent is extended or adjusted under 35 U.S.C. 154(b) by 437 days.

(21) Appl. No.: 14/039,660

(22) Filed: Sep. 27, 2013

(65) Prior Publication Data
US 2014/0094851 A1 Apr. 3, 2014

Related U.S. Application Data

(60) Provisional application No. 61/744,525, filed on Sep. 28, 2012.

(51) Int. Cl.
*A61B 17/70* (2006.01)
*A61B 17/80* (2006.01)

(52) U.S. Cl.
CPC ...... *A61B 17/7022* (2013.01); *A61B 17/7001* (2013.01); *A61B 17/701* (2013.01); *A61B 17/7002* (2013.01); *A61B 17/705* (2013.01); *A61B 17/7007* (2013.01); *A61B 17/7053* (2013.01); *A61B 17/7055* (2013.01); *A61B 17/809* (2013.01); *A61B 17/7067* (2013.01); *A61B 17/7068* (2013.01)

(58) Field of Classification Search
CPC ............ A61B 17/7044; A61B 17/7055; A61B 17/7019; A61B 17/7022; A61B 17/7031; A61B 17/842; A61B 17/8645
See application file for complete search history.

(56) References Cited

U.S. PATENT DOCUMENTS

| 4,448,191 | A | 5/1984 | Rodnyansky |
| 5,147,360 | A | 9/1992 | Dubosset |
| 5,290,289 | A | 3/1994 | Sanders et al. |
| 5,490,851 | A | 2/1996 | Nenov et al. |
| 6,299,613 | B1 | 10/2001 | Ogilvie et al. |
| 2005/0149019 | A1* | 7/2005 | Sasing ............... A61B 17/7049 606/250 |
| 2006/0047282 | A1* | 3/2006 | Gordon .............. A61B 17/7016 606/86 A |
| 2008/0021456 | A1 | 1/2008 | Gupta et al. |

(Continued)

FOREIGN PATENT DOCUMENTS

| EP | 2449939 A1 | 5/2012 | |
| FR | 2781359 A1 * | 1/2000 | ......... A61B 17/7043 |
| WO | 2012072413 A1 | 6/2012 | |

OTHER PUBLICATIONS

Translation of FR 2781359; accessed from EPO.org on May 7, 2016.*

(Continued)

*Primary Examiner* — Julianna N Harvey

(57) ABSTRACT

The present invention generally relates to methods and device for treatment of spinal deformity, wherein at least one tether is utilized to maintain the distance between the spine and the an ilium to (1) prevent increase in abnormal spinal curvature, (2) slow progression of abnormal curvature, or (3) impose at least one corrective displacement and/or rotation.

13 Claims, 15 Drawing Sheets

(56) References Cited

U.S. PATENT DOCUMENTS

2009/0270920 A1* 10/2009 Douget .............. A61B 17/7055
606/254
2009/0281575 A1  11/2009 Carls et al.
2010/0106195 A1   4/2010 Serhan et al.
2012/0150231 A1*  6/2012 Alamin .............. A61B 17/1606
606/263

OTHER PUBLICATIONS

International Search Report and Written Opinion for International Application No. PCT/US2013/062502 dated Sep. 28, 2013.

* cited by examiner

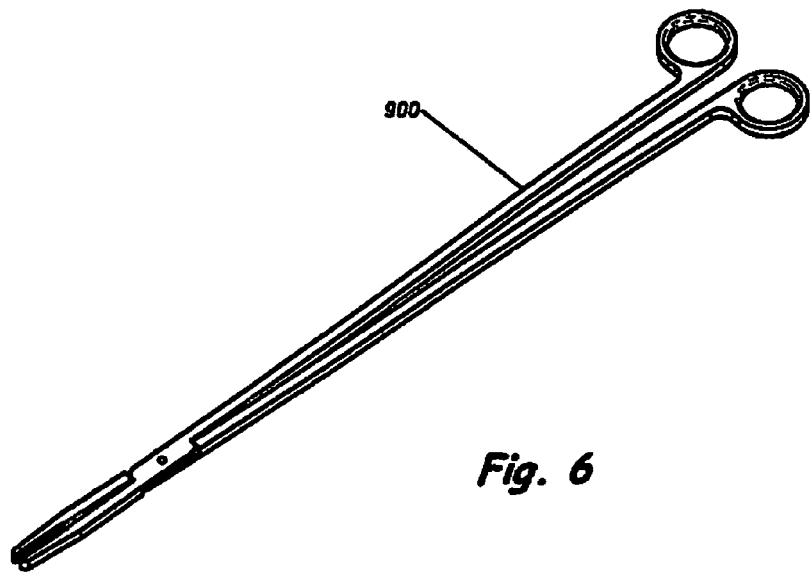
Fig. 6
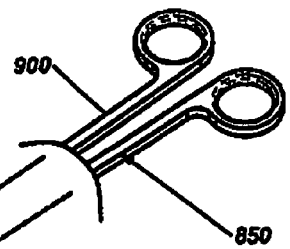
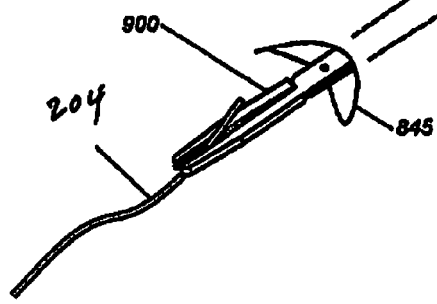
Fig. 7

DEVICE AND METHOD FOR TREATMENT OF SPINAL DEFORMITY

CROSS-REFERENCE TO RELATED APPLICATIONS

This patent application is non-provisional application which claims priority to U.S. Provisional Application Ser. No. 61/744,525 filed on Sep. 28, 2012, which is incorporated in its entirety herein.

FIELD OF THE INVENTION

The present invention generally relates to methods and devices for treatment of spinal deformity.

BACKGROUND OF THE INVENTION

Scoliosis is a spinal deformity characterized by an abnormal curvature of the spine in the coronal plane. Adolescent idiopathic scoliosis (AIS) is the most prevalent type of scoliosis which develops during adolescence in an otherwise healthy patient and typically ceases at the onset of skeletal maturity. The cause of the disease is presently unknown.

Current surgical treatment of scoliosis involves manipulation of the spinal column and attachment of corrective devices for fusion of a portion of the spine. One such system, the Cotel-Dubousset system utilizes rigid metal rods attached to the spine. The rods are manipulated during surgery in an attempt to reduce abnormal curvatures and rotations of the spinal column. Large loads are exerted on the spine for correction which risks the patient's neurological condition. Recovery from these procedures can be lengthy and painful. Also, if normal lordosis and kyphosis are not restored, a condition called "flat back syndrome" may occur causing chronic pain. Even a successful procedure rarely results in a normal spinal curvature and the patient is left with an immobile spinal section. The discs above and below the fusion zone are at risk of future degeneration due to the increased mechanical demands placed on them.

It is therefore evident that there are flaws in prior art methods and devices. Most prior art devices are part of the load path of the spinal column. For example, it is understood that the Cotel-Dubgousset system rigidly attaches stiff metal rods to the spine. A structure having two roughly parallel support members relies primarily on the stiffer of the two members for transmission of loads. Therefore, loads exerted on an instrumented spine are transferred through the implant instead of through the spine. Spinal loads can be significantly large, and the implants will not support such loads indefinitely. Fatigue failure of the implant will occur if fusion is delayed.

Therefore, there is an unaddressed need that exists to provide a new and better system for correcting spinal deformities.

SUMMARY OF THE INVENTION

The current invention describes methods and devices for treating spinal deformity which offer significant improvements over prior art methods and devices. In general terms the present invention is used to secure the distance between an ilium and the spine to either correct or maintain spinal curvature. There are many embodiments of the invention which will achieve the stated objectives, some of which will be presented in the following summary.

In one embodiment of the invention, at least one device is attached between the spine and the pelvis which incorporates at least one flexible tether. Attachment of the flexible tether to the spine and ilium involves implantation of anchoring means and then attachment of the tether to the anchoring means. For example, at least one bone screw, pedicle screw, cannulated bone screw, clamp, plate, bone anchor, or shackle might be anchored to at least one vertebra and another to a portion of the ilium and the flexible tether may be attached to both. Other means of attachment will be clear to one practiced in the art. Alternatively, a loop of material may be placed around a bony structure (e.g. spinous process, transverse process, lamina or pars) or a hole through a bony structure through which the flexible tether is passed.

It should be noted that the present invention enables manipulating the vertebral column to correct the deformity by securing the tether to a portion of the ilium and a portion of the vertebral column; the ability to correct deformity by correcting the effective length of the tether between the ilium and vertebra over time; and correcting deformity by the natural growth of the spine by allowing the tether to maintain effective length between the vertebral column and the ilium.

Adjustment of the distance between the spine and ilium is achieved by varying the location at which the tether is attached to the anchoring means. The tether does not change lengths during the adjustment process, but the distance between the attachment points does, much like adjusting a belt around your waist. Taking advantage of the inherent viscoelasticity of spinal structures, the curvature may be gradually corrected by small incremental corrections over a protracted period of time, whereby the original incision is re-opened, or a new incision next to the original incision is created and the attachment means is disengage and then reengaged at a different location along the tether. Alternatively the patient's growth may be used to achieve correction.

Alternatively, the tether may branch into multiple tethers to provide multiple attachments to the spine and/or ilium. If more than one tether is used, each can be attached to a different vertebra, or multiple tethers can be attached to the same vertebra. Tethers can be attached to either or both sides of the vertebral column and either opposing sides of ilium as needed to generate correction of the spinal deformity. A crossing pattern whereby a tether is attached to the right side of the vertebra (e.g. the right pedicle) and left ilia, or vice versa, is possible. Also, a tether may be attached to a vertebra and then passed through an eye screw or other guiding device which is attached to the ilium (or both ilia) and then attached to a second vertebra with a pedicle screw or other means. In can be envisioned by one skilled in the art that guiding devices may be utilized on a number of vertebrae or one the ilium or ilia. The tether may also originate with an attachment to the pelvis, pass through any number of guide members attached to the spine, and then terminate at the pelvis again.

These and other aspects of the present invention, will become apparent from the following description of the embodiments taken in conjunction with the following drawings, although variations and modifications therein may be affected without departing from the spirit and scope of the novel concepts of the disclosure.

The present invention provides an improved method of arresting a spinal deformity whereby at least one device is surgically attached between the spine and the ilium. Also, the present invention provides a system and a method for correcting a spinal deformity whereby at least one device is surgically attached between the spine and the ilium.

BRIEF DESCRIPTION OF THE DRAWINGS

The present invention will become more fully understood from the detailed description and the accompanying drawings, wherein:

FIG. 6 shows a long pair of forceps to be used for passing the tether beneath the skin;

FIG. 7 illustrates the use of the forceps of FIG. 6 in passing the tether beneath the skin;

DETAILED DESCRIPTION OF THE PREFERRED EMBODIMENTS

The following description of the preferred embodiment(s) is merely exemplary in nature and is in no way intended to limit the invention, its application, or uses. The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

Figure 1:
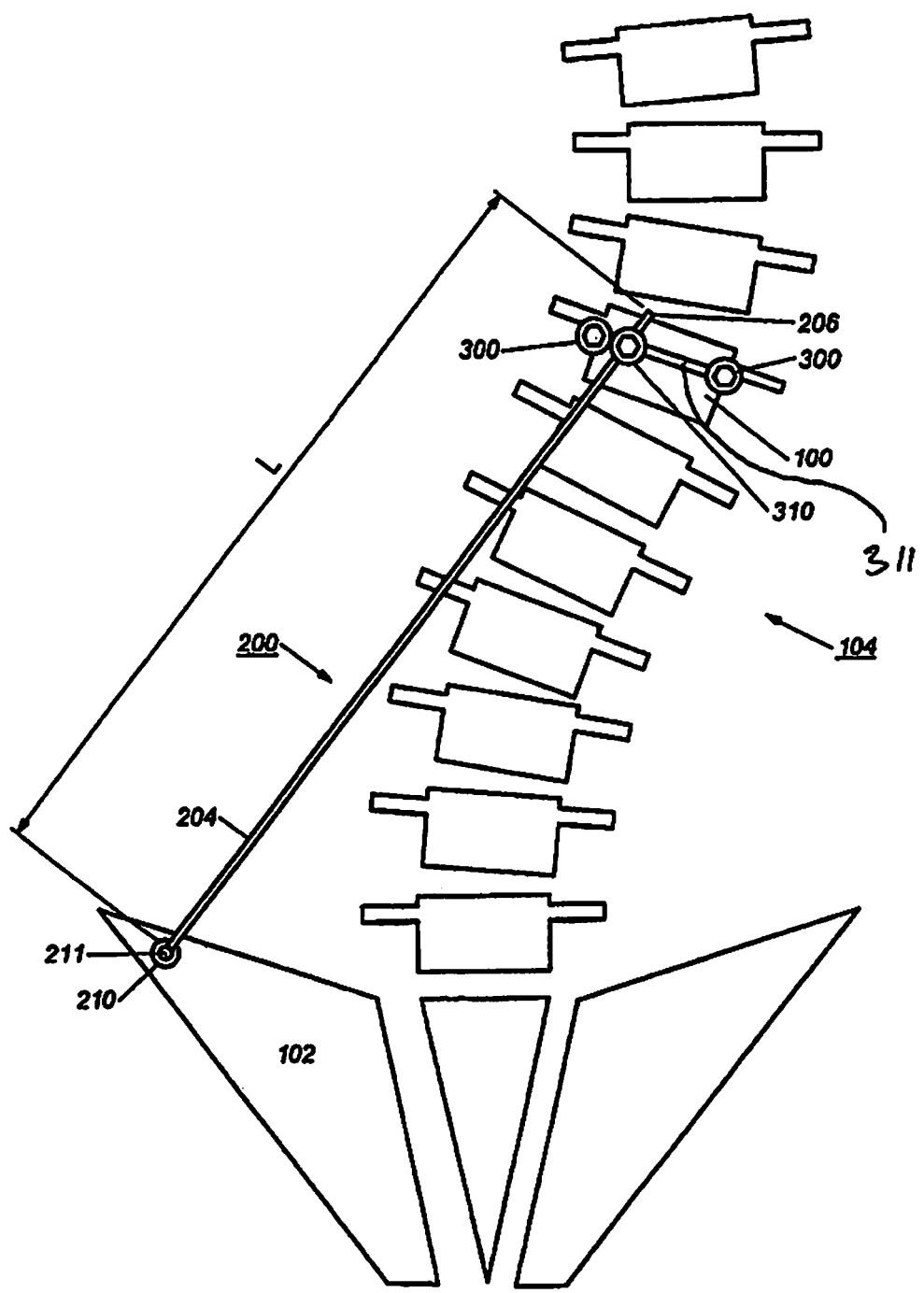
FIG. 1 is an illustration of a posterior view of a deformed human spine with an implanted device according to one embodiment of the present invention.

FIG. 1 is an illustration of a posterior view of a deformed spine 104 whereby the preferred embodiment of the device 200 is attached to an ilium 102 and a vertebra 100. Device 200 includes a tether 204 having a free end 206 and that is configured to be attached to the ilium and a portion of the vertebra. Specifically, in one embodiment, two attachment mechanisms such as pedicle screws 300 are anchored to the vertebra of the spine by insertion into opposing pedicles, and a transverse rod 311 is attached to the pedicle screws 300. It should be noted that although pedicle screws are provided in this particular embodiment, any other type of anchoring mechanism such as hooks may also be used. A tether clamp 310 is attached to rod 311 and the tether 204 is passed though tether clamp 310 and then passed down to the ilium 102 thereby securing a connection between the attached vertebra and the ilium. To attach the tether 204 to the ilium 102, an ilium anchor 210 is provided. The ilium anchor 210 includes a bore 211 and is configured to be attached to the ilium by inserting the anchor 210 (threading) into a hole which has been drilled or punched through the ilium 102. It should be noted that any other similar mechanism to attach anchor 210 to the ilium 102 may also be utilized. Tether 204 is passed through hole or bore 211 in the ilium anchor 210 and then brought back to the vertebra 100 and passed again through the tether clamp 310. In other embodiments, the tether 204 may only be passed once through the tether clamp and ilium anchor 210.

Figure 2:
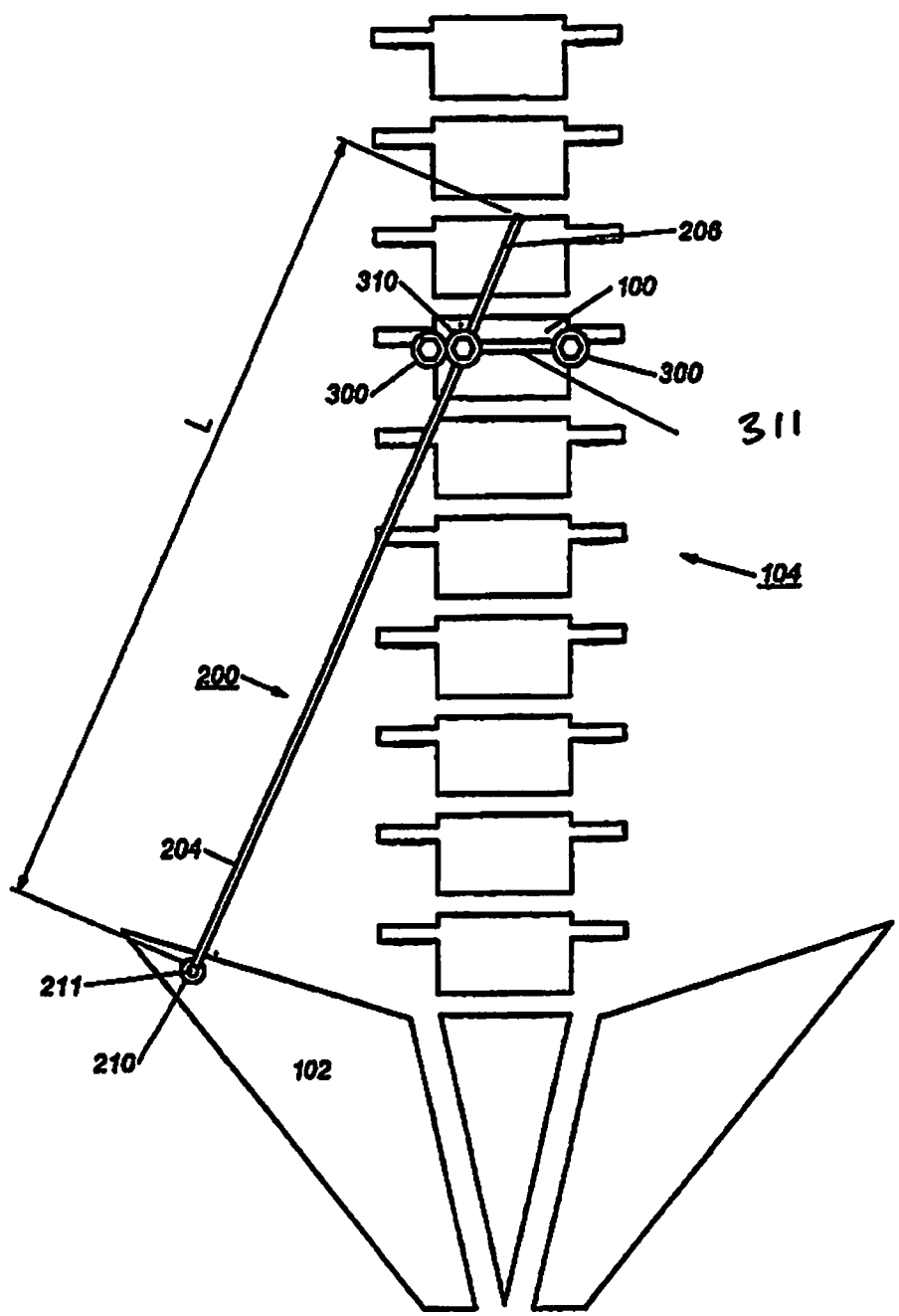
FIG. 2 is an illustration of a posterior view of a corrected human spine with the implanted device shown in FIG. 1.

FIG. 2 illustrates the correction of the spine of FIG. 1 using device 200. As illustrated in FIG. 2, the free end 206 of tether 204 is pulled and the spine is manually manipulated during the surgery to achieve a correction of the deformity. When a satisfactory curve magnitude is achieved, tether 204 is tightened within the tether clamp, effectively locking the distance between vertebra 100 and the ilium 102.

It should be noted that various levels of manipulation of the vertebral column can be coordinated using the device. For instance, different curvatures of the spine can be achieved by changing the position of the anchor and the clamp on the tether with respect to the vertebral column and the ilium. The locations along the tether where the clamp and anchor are attached determine an effective length of the tether, which in turn maximizes the distance that the attached vertebra may move relative to the position where the tether is attached at in the ilium. The scoliotic curve is corrected (or maintained) by adjusting the clamping and anchoring locations along the tether.

Figure 3:
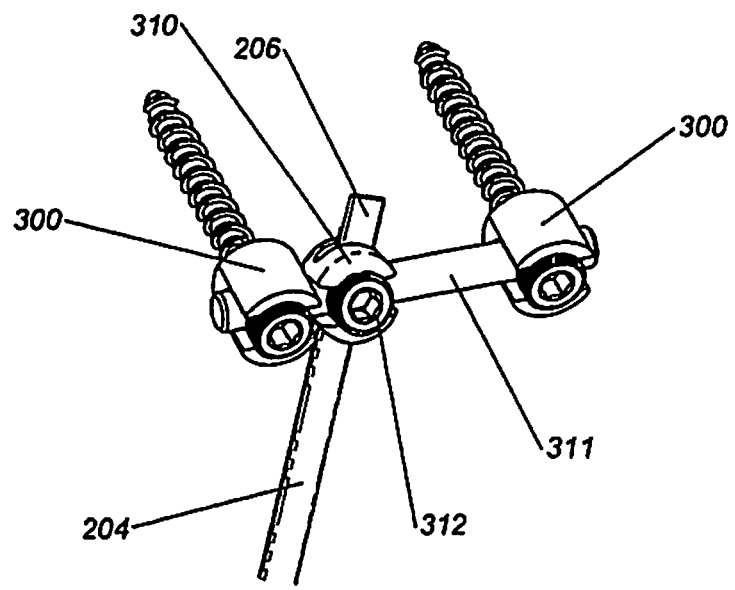
FIG. 3 shows a spinal anchoring means in the form of two pedicle screws and a rod onto which is secure an attachment mechanism and the tether.

FIG. 3 shows a detailed view of pedicle screws 300, transverse rod 311, tether clamp 310 and tether 204. In a preferred embodiment tether clamp 310 includes locking screw 312 which clamps tether clamp 310 onto rod 311 as well as locking the tether 204 within the clamp 310.

Figure 4:
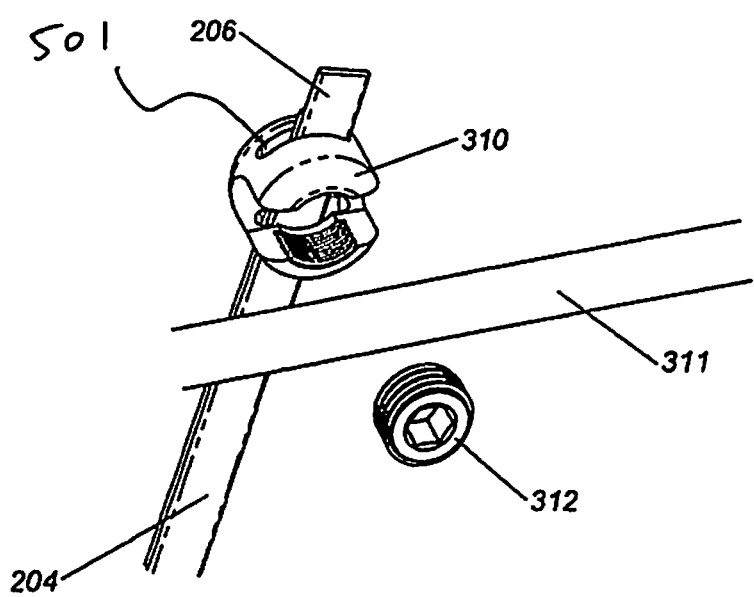
FIG. 4 illustrates an attachment mechanism and the method of attaching it to the spinal anchoring mechanism.

FIG. 4 shows a detailed view of the tether clamp 310 coupled to the transverse rod. The tether clamp 310 is configured with a slot 501 which is provided through the tether clamp 310 and tether 204 is passed through slot 501. It should be noted that the tether may be passed through the slot multiple times, if necessary. Locking screw 312 is used to secure the transverse rod 311 onto the tether clamp 310 and applies a compressive force upon the rod 311 onto the tether 204, thereby clamping the tether 204 securely in place. It should be noted that although a threaded set screw is utilized in the present embodiment, any type of locking element know in the art for securing the tether within tether clamp may be used.

Figure 5:
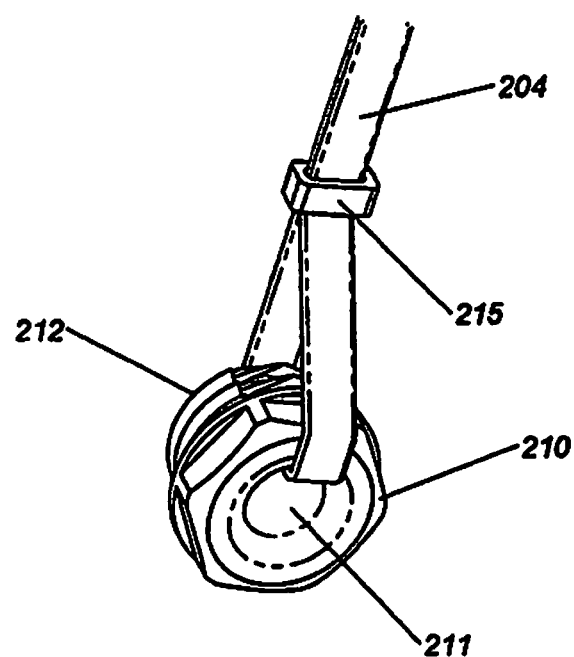
FIG. 5 shows the anchoring mechanism of the ilium (not shown) and the method of attaching the tether to it.

FIG. 5 shows a detailed view of an ilium anchor 210. Ilium anchor 210 includes threads 212 for engagement with ilium 102 (not shown). Tether 204 is passed through bore 211 and then passed back to the vertebral column. A collar 215 is shown which keeps tether 204 adjacent to itself.

FIG. 6 shows an extra-long pair of forceps 900. FIG. 7 shows the preferred method of passing the tether through an incision 845 and underneath skin and other soft tissues. The forceps 900 are used to pass the tether though the openings in the tether clamp and used to tension the tether to correct the deformity of the curvature in the spine.

Figure 8:
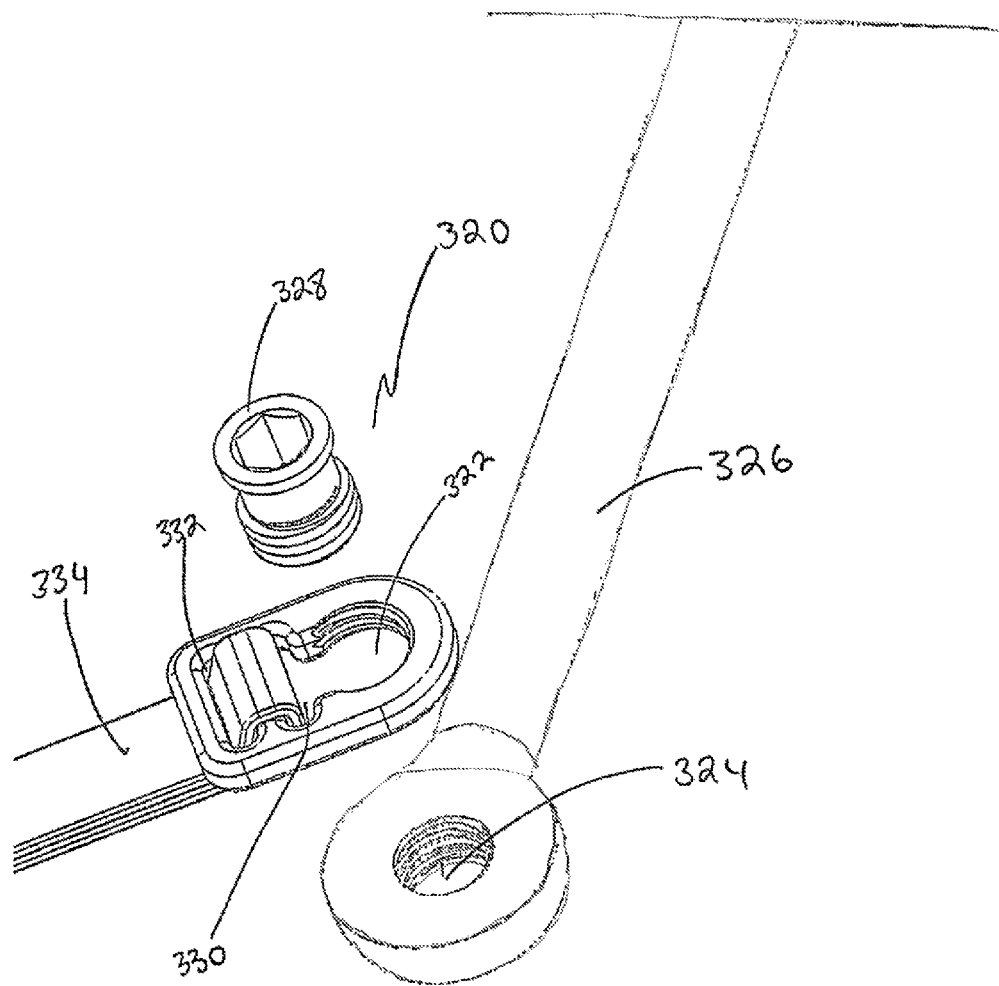
FIG. 8 illustrates an alternative embodiment of the tether clamp and elongate rod according to the present invention.

FIG. 8 illustrates another embodiment of a tether clamp 320 according to the present invention. In this embodiment, the tether clamp 320 is configured with a through hole 322 that is configured to correspond to a through hole 324 in an elongate rod 326 that is fixated to a portion of the spinal column. A fastening element 328 such as a set screw is provided to couple the tether clamp 320 and the elongate rod 326 together. The tether clamp 320 also includes openings 330, 332 which are dimensioned to receive and securely couple a tether 334 to the clamp 320. The tether 334 is pulled through each of the openings 330, 332 to securely attach the tether 334 to the clamp 320 and the elongate rod 326.

Figure 9:
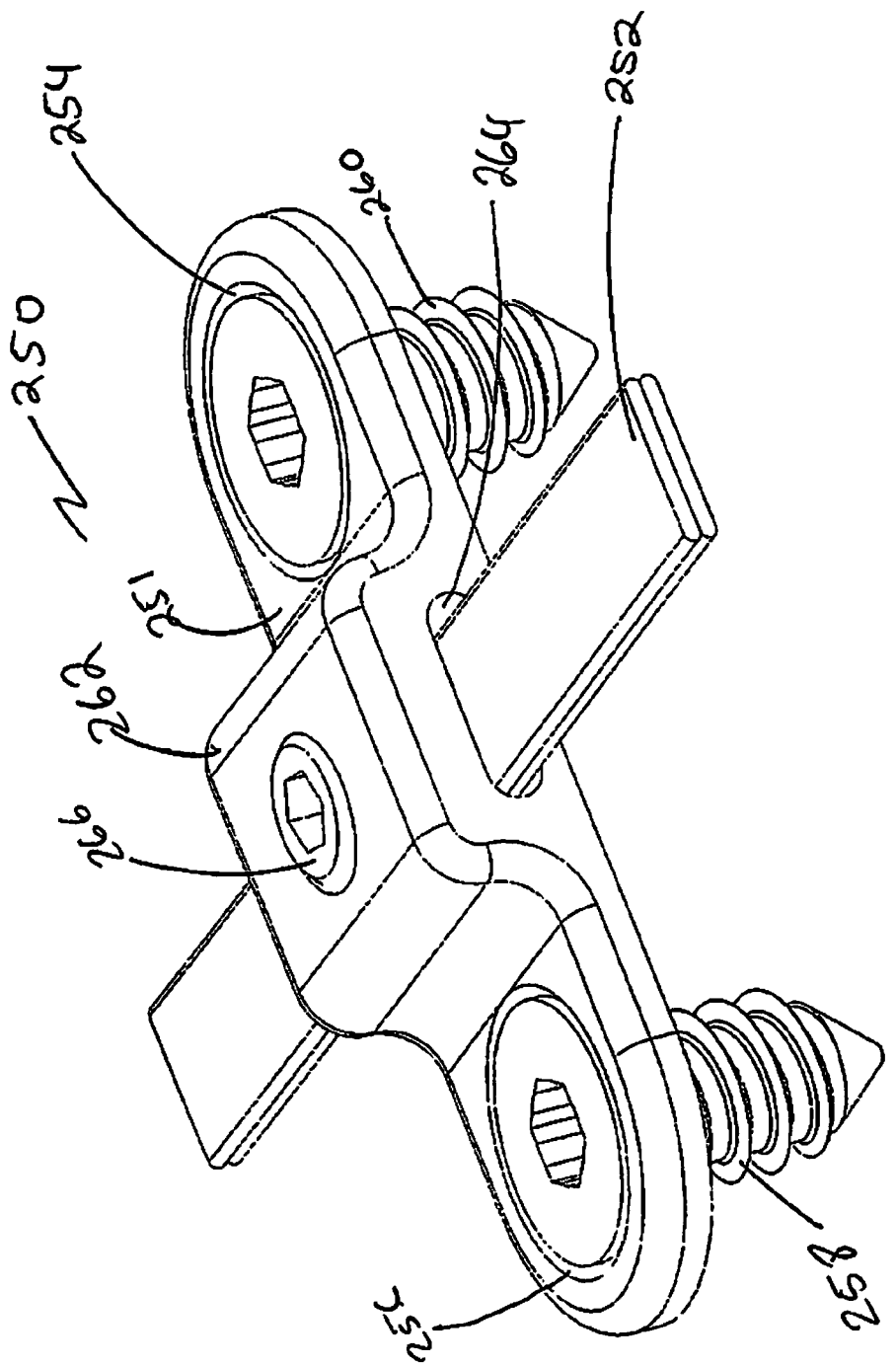
FIG. 9 illustrates another embodiment of a clamp or anchor according to the present invention.
Figure 10:
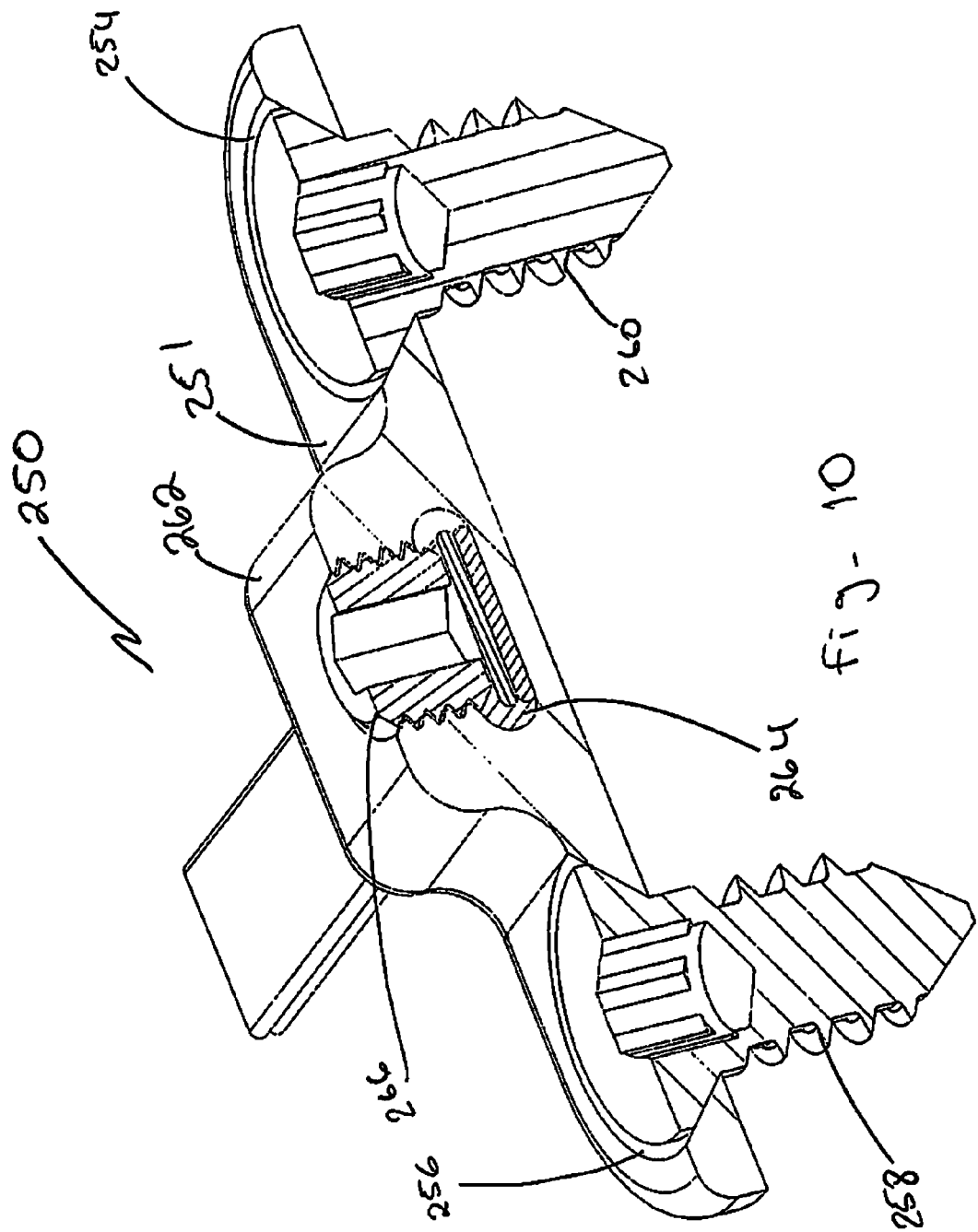
FIG. 10 shows a cross-sectional view of the device shown in FIG. 9.

FIGS. 9 and 10 illustrate an alternative embodiment of a clamp and/or anchor 250 that can be used to secure a tether 252 to either the vertebral column or a portion of the ilium. More specifically, the anchor 250 of FIGS. 9 and 10 may be configured and dimensioned to be attached to a portion of the vertebral column or may be configured be secure the tether to the ilium. The anchor 250 is configured as a plate 251 having at least two openings 254, 256 to receive fasteners 258, 260 capable of fixating the plate to bone. The plate 251 includes a middle portion 262 having an opening 264 that is capable of receiving the tether 252. The middle portion 262 of the plate 251 is further provided with a fastening element 266 to secure the tether 252 to the plate 251. As more clearly illustrated in FIG. 10, the fastening element 266 may be a set screw which directly contacts the tether 252 when tightened to secure the tether 252 to the plate 251. It should be noted that any other type of fastening element which is capable of securing the tether to the anchor may be used, such as a pin.

Figure 11:
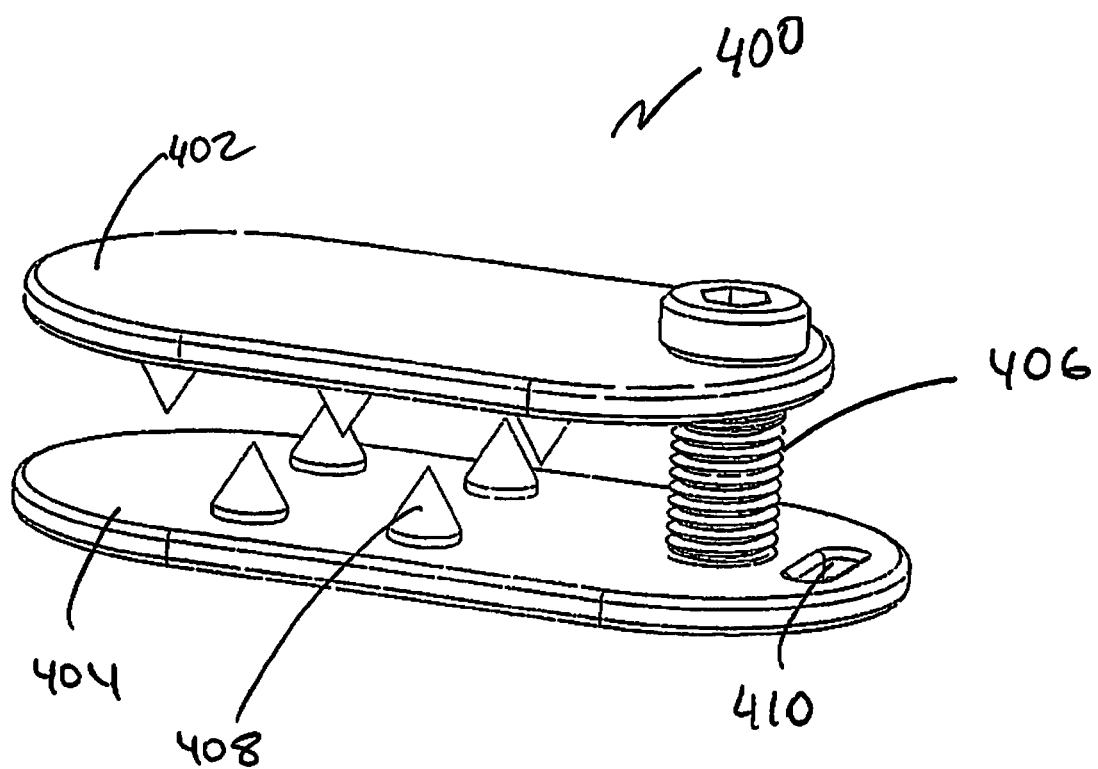
FIG. 11 shows another embodiment of a clamp or anchor according to the present invention.

FIG. 11 illustrates yet another embodiment of a clamp or anchor 400 according the present invention. In this embodiment, the clamp and/or anchor 400 includes a first plate 402 and second plate 404 that are secured to one another via a fastening element 406. The first and second plates 402, 404 are may also include spikes 408 or similar type of features that bite into bone. Either the first or second plate 402, 404 or both also includes an opening 410 for receiving a tether. The first and second plates 402, 404 are positioned so that bone is in between, such as the ilium or a portion of the vertebral column. As the first and second plates 402, 404 are compressed into bone, the tether which is positioned through the opening 410 and in between the first and second plates 402, 404, is also securely locked between the plates and the bone thereby securing the tether to the plates 402, 404. In an alternative embodiment, the tether is passed through the opening and secured to the anchor 400 by a clamp device such a belt clamp or secured by knotting the tether around the edge of the anchor 400. It should be noted that any type of mechanical mechanism to attach the tether to the anchor may be used.

Figure 12:
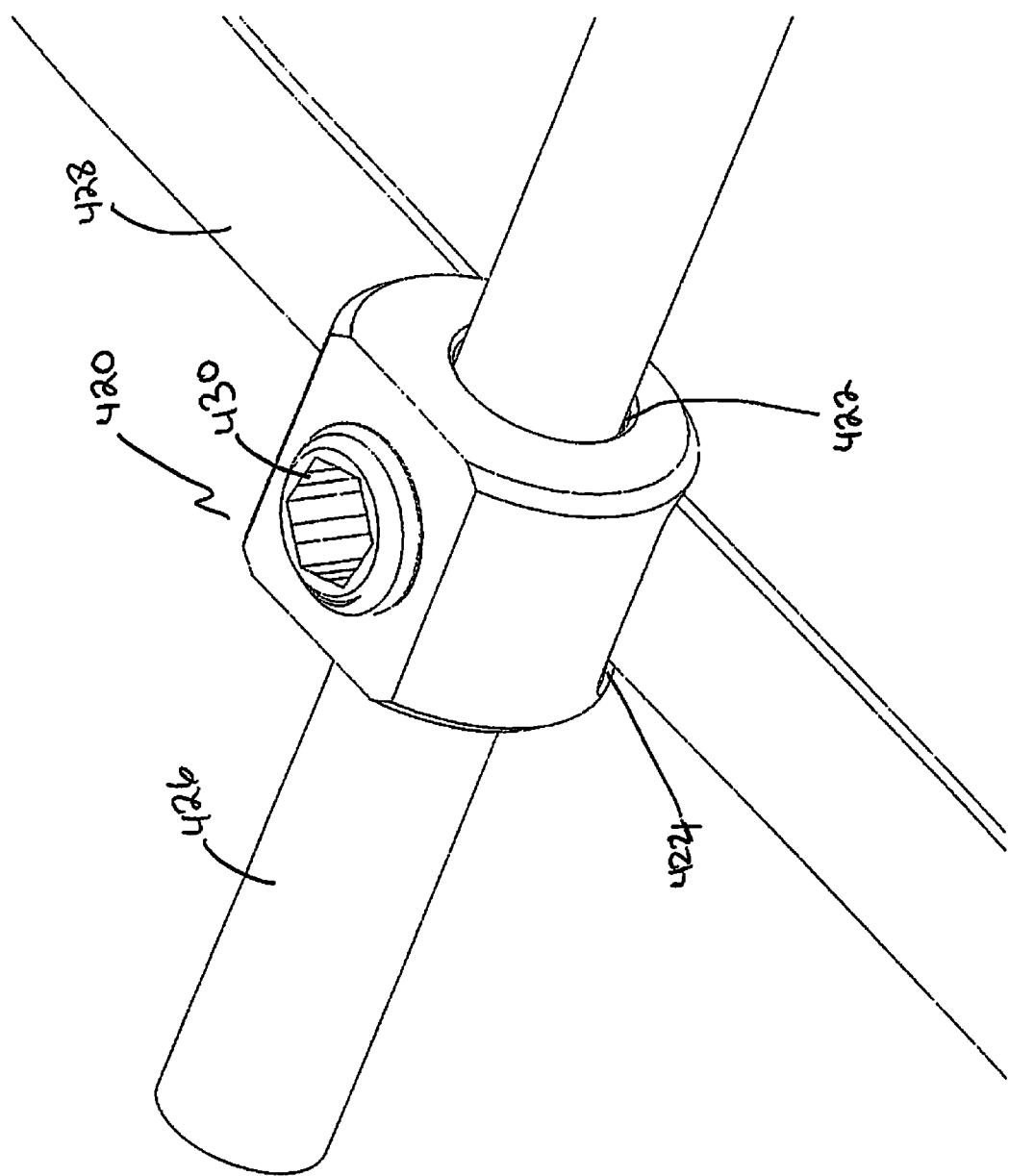
FIGS. 12 and 13 shows a closed head clamp according to the present invention.
Figure 13:
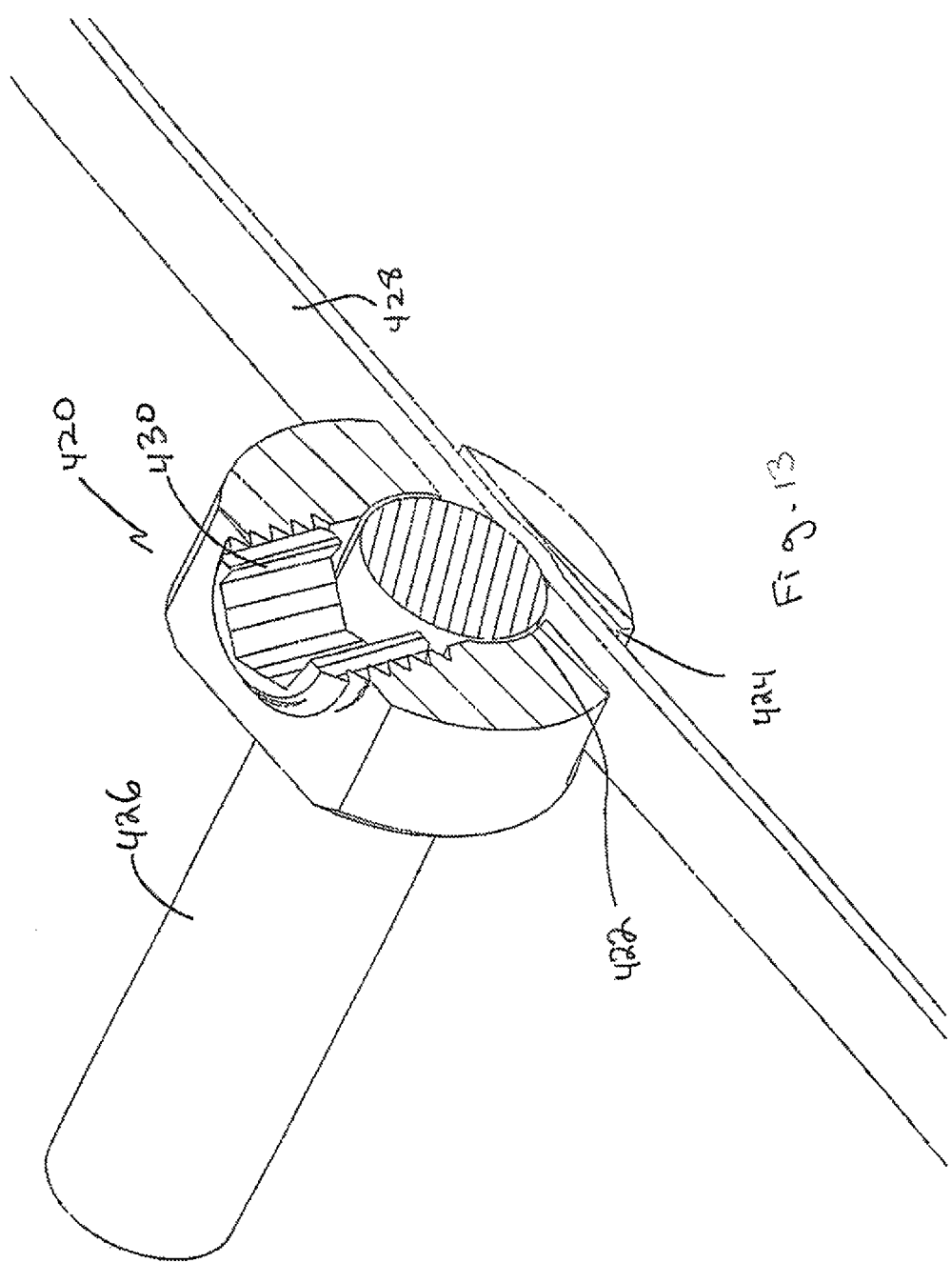

FIGS. 12-15 illustrate yet another embodiment of a clamp according to the present invention. The closed head clamp 420 as illustrated in FIGS. 12 and 13, includes a first opening 422 extending through the clamp 420 in a first direction and a second opening 424 extending in a second direction. The first and second direction are generally perpendicular to one another. The first opening 422 is configured to receive an elongate rod 426 and the second opening 424 is configured to receive a tether 428. The clamp 420 is further provided with a fastening element 430 that is used to secure both the rod 426 and the tether 428. In this embodiment, FIGS. 12 and 13 also illustrates that the second opening 424 is positioned at a bottom portion of the clamp 420, thus, as the fastening element 430 is tightened, the fastening element 430 contacts the rod 426 which is pushed against the tether 428 thereby securing the tether 428 and rod 426 within the clamp.

Figure 14:
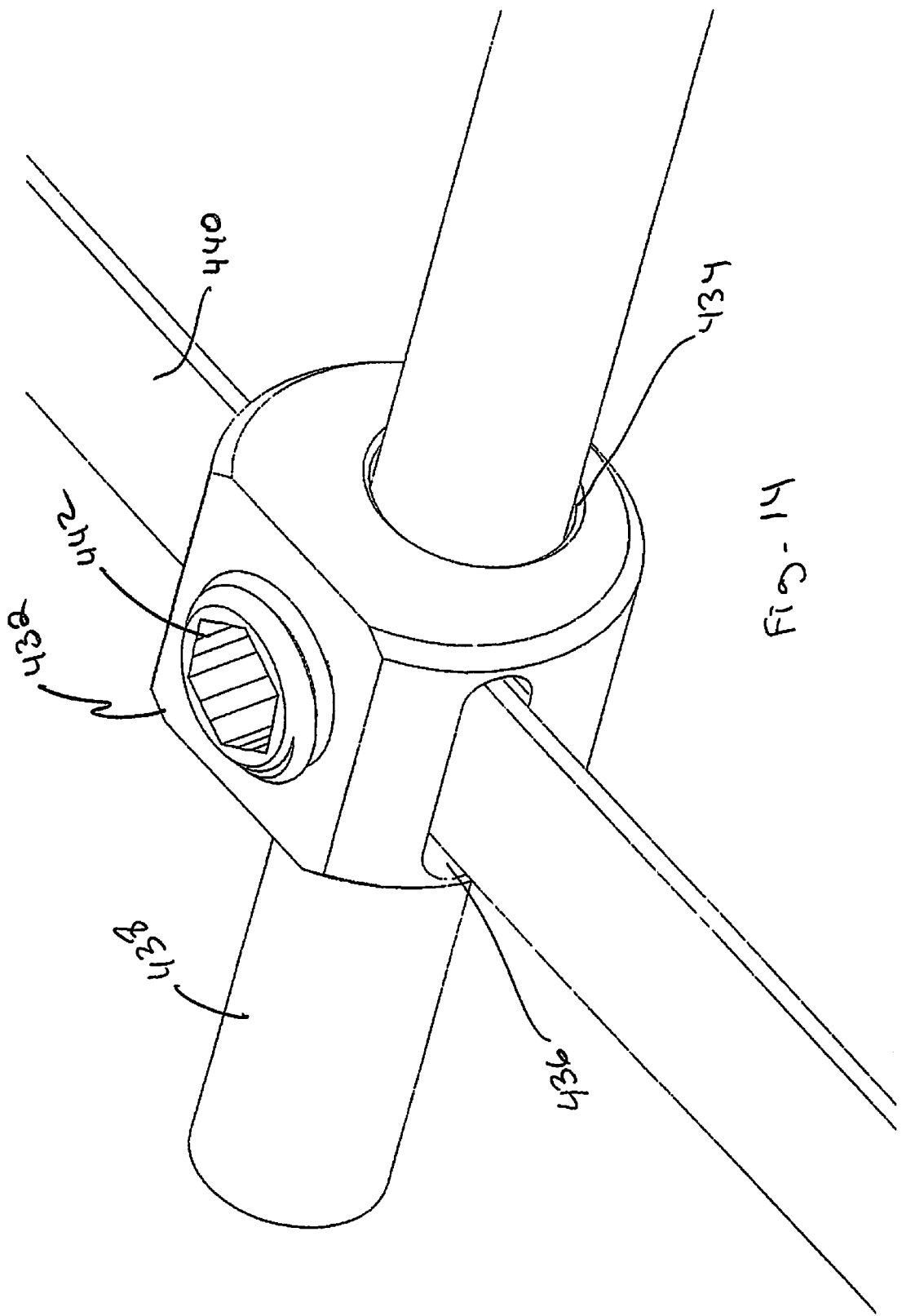
FIGS. 14 and 15 shows yet another embodiment of a closed head clamp according to the present invention.
Figure 15:
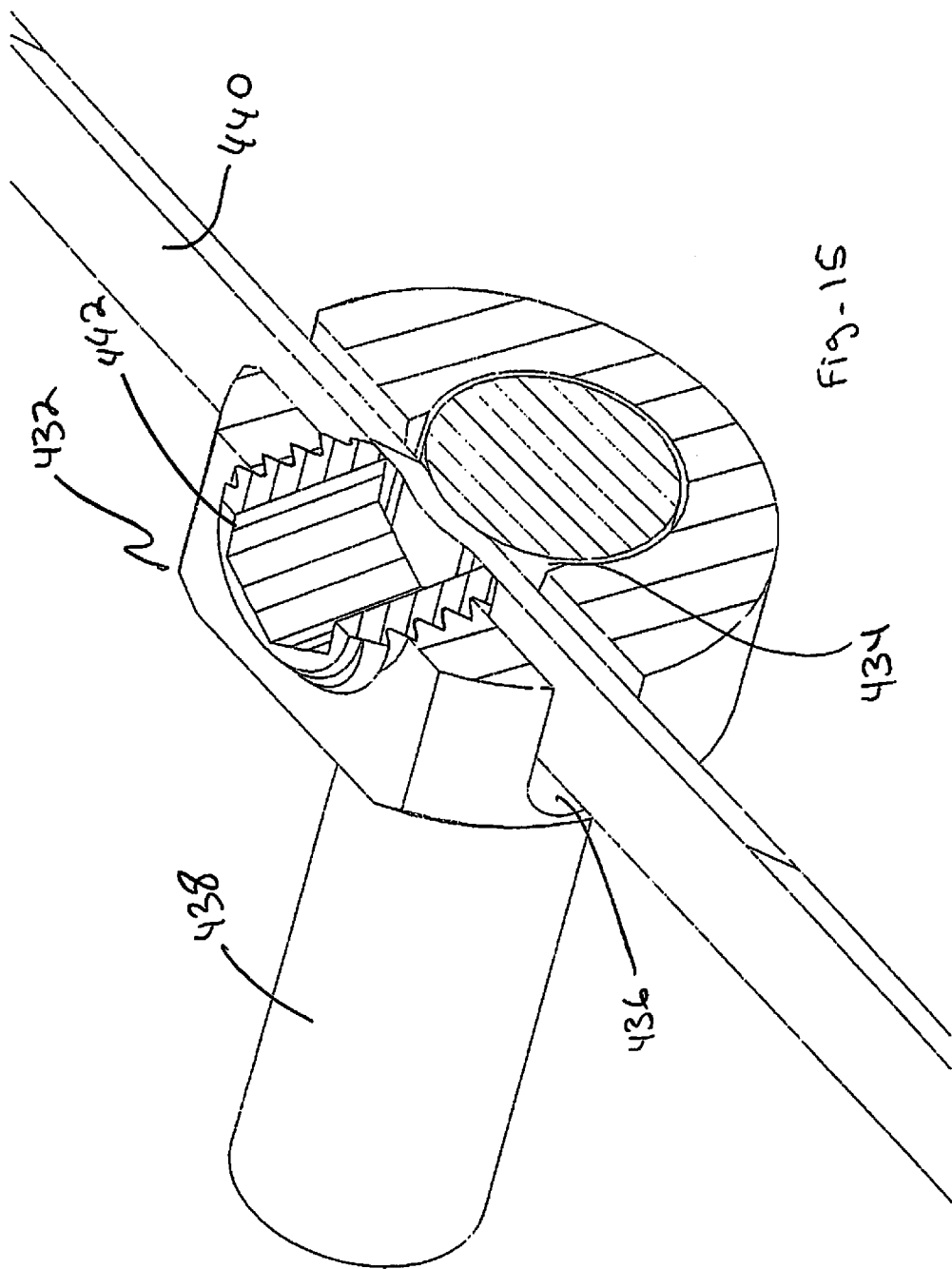

In an alternative embodiment of the closed head clamp as illustrated in FIGS. 14 and 15, the closed head clamp 432 includes a first opening 434 and a second opening 436. The first opening 434 and the second opening 436 are configured to be generally transverse to one another. The first opening 434 is dimensioned to receive an elongate rod 438 and the second opening 436 is dimensioned to receive a tether 440. The clamp 432 also includes a fastening element 442, such as a set screw, which when tightened secures and locks the tether 440 and the elongate rod 438 within the clamp 432. In this particular embodiment, the second opening 436 is positioned between the fastening element 442 and the elongate rod 438. When the fastening element 442 is tightened, the fastening element 442 directly contacts the tether 440 which contacts the elongate rod 438 thereby securely locking the tether 440 and the elongate rod 438 within the closed head clamp 432.

Figure 16:
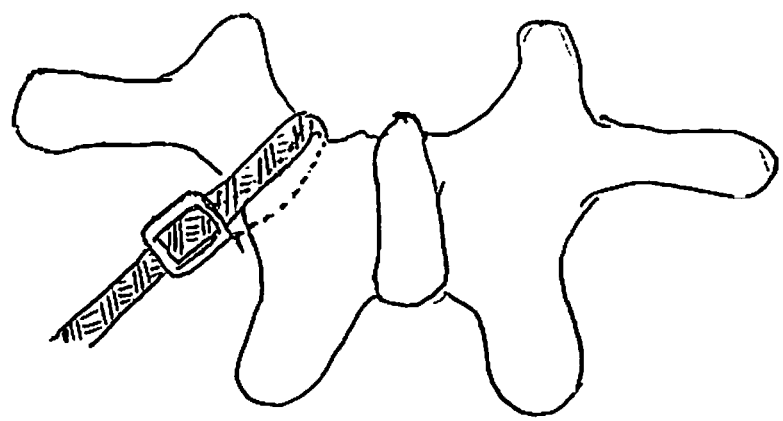
FIGS. 16-18 illustrate various methods of coupling the tether to portions of the spine and/or ilium.
Figure 17:
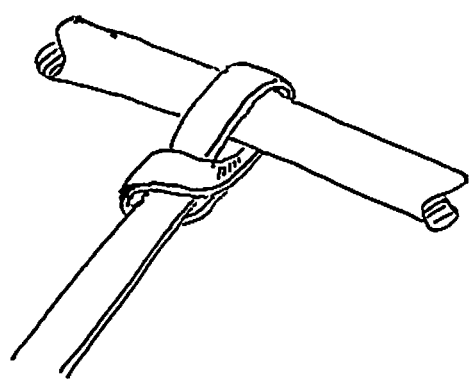
Figure 18:
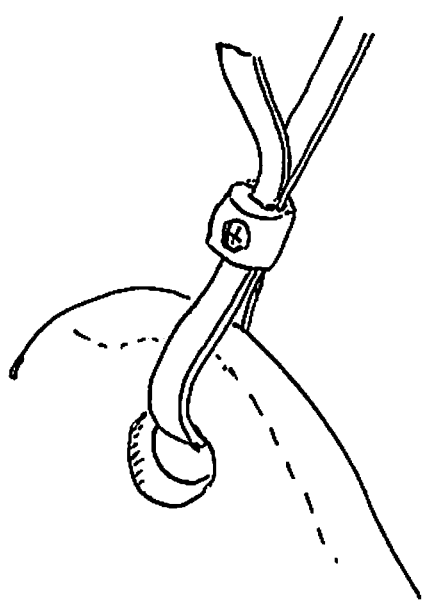

FIGS. 16-18 illustrate alternative embodiments of the inventive device. Specifically, FIG. 16 illustrates the use of clamp to attach the tether to the lamina of a vertebra. As illustrated, the tether may encircle the lamina and may be tightened using a belt clamp. The other end of the tether is as shown in the earlier embodiments coupled to a portion of the ilium. Using this mechanism, the deformity of the spine may be corrected by manipulating the tether as well as the positioning of the clamp, as needed.

FIG. 17 shows a tether that includes a loop which is used to for coupling the tether to the transverse rod to fixate the tether to the transverse rod. FIG. 18 illustrates the coupling of the tether directly to the ilium using another type of tether clamp. It should be noted that in the examples provided of both anchor and clamps, these mechanical devices may be interchangeable.

It should also be noted that the tether of the present invention may be composed of fabric, polymer, such as PET, or any other biocompatible materials. The tether can be a cable and can be dimensioned to be a wide elastic band which advantageously reduce the risk of damage to tissue lacerations or injury. In some embodiments, the tether can be is between 2 and 900 mm. Also, to ensure that proper correction of deformities, a tensioner can be included as part of the system to make sure that the tether are in proper tension and tightness.

It will be apparent to those skilled in the art that various modifications and variations can be made in the present invention without departing from the scope or spirit of the invention. Moreover, the improved bone screw assemblies and related methods of use need not feature all of the objects, advantages, features and aspects discussed above. Thus, for example, those skilled in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or subcombinations of these specific features and aspects of embodiments may be made and still fall within the scope of the invention. Accordingly, it should be understood that various features and aspects of the disclosed embodiments can be combined with or substituted for one another in order to form varying modes of the discussed bone screw assemblies. Thus, it is intended that the present invention cover the modifications and variations of this invention provided that they come within the scope of the appended claims or their equivalents.

What is claimed is:

1. A spinal system comprising:
   a clamp for receiving an elongate rod therein, wherein the clamp comprises a first opening for receiving the elongate rod, and a second opening transverse to the first opening for receiving a first portion of a tether, wherein the first opening that receives the elongate rod is formed on an upper surface of the clamp such that the elongate rod is downwardly delivered therein;

a fastener downwardly received in the first opening formed on the upper surface of the clamp, wherein the elongate rod is positioned between the tether and the fastener such that the fastener is not in direct contact with the tether;

an anchor configured to be implanted in the ilium, the anchor having a bore hole receiving a second portion of the tether, wherein when the anchor is implanted in the ilium, the tether extends from one side of the ilium to the other side of the ilium, wherein when the fastener is actuated into the first opening, the elongate rod positioned in the first opening and the tether positioned in the second opening, the elongate rod contacts and compresses the tether, thereby securely locking the elongate rod and tether within the clamp.

2. The system of claim 1, wherein the clamp is positioned on the elongate rod between two bone fasteners.

3. The system of claim 1, wherein the clamp can be moved laterally on the elongate rod prior to tightening of the fastener.

4. The system of claim 1, wherein the fastener is a set screw.

5. The system of claim 1, wherein when the fastener is tightened the fastener applies a force against the elongate rod which applies a force against the tether to securely lock both the tether and the elongate rod within the clamp.

6. The system of claim 1, wherein the anchor includes threads for engagement to the ilium.

7. The system of claim 1, wherein the second portion of the tether is passed through the bore hole of the anchor and coupled to a collar.

8. The spinal system of claim 1, wherein the positioning of the clamp or anchor is configured to modify the curvature of the spine.

9. A spinal system comprising:
a clamp for coupling to an elongate rod, wherein the clamp comprises a first opening for receiving the elongate rod and a second opening for receiving a tether, wherein the first opening that receives the elongate rod is formed on an upper surface of the clamp such that the elongate rod is downwardly delivered therein;

a fastener downwardly received in the first opening formed on the upper surface of the clamp for securing the tether to the elongate rod, wherein the elongate rod is positioned between the tether and the fastener such that the fastener is not in direct contact with the tether;

an anchor configured to be implanted in the ilium, the anchor having a bore hole receiving a second portion of the tether, wherein when the anchor is implanted in the ilium, the tether extends from one side of the ilium to the other side of the ilium, wherein when the fastener is actuated into the first opening, the elongate rod contacts and compresses the tether, thereby securely locking the elongate rod and tether within the clamp, and the tether is securely positioned between a portion of a vertebral column and the ilium.

10. The spinal system of claim 9, wherein the fastener is a set screw.

11. The spinal system of claim 9, wherein the tether is looped through the second opening of the clamp.

12. The spinal system of claim 9, wherein the elongate rod is extendable from laterally across the spinal column.

13. A spinal system comprising:
a clamp for coupling to an elongate rod and wherein the clamp comprises a first opening for receiving a fastener and a second opening for receiving a tether, wherein the first opening that receives the elongate rod is formed on an upper surface of the clamp such that the elongate rod is downwardly delivered therein;

a fastener downwardly received in the first opening formed on the upper surface of the clamp for securing the tether to the elongate rod, wherein the elongate rod is positioned between the tether and the fastener such that the fastener is not in direct contact with the tether;

an anchor configured to be implanted in the ilium, the anchor having a bore hole receiving a second portion of the tether, wherein when the anchor is implanted in the ilium, the tether extends from one side of the ilium to the other side of the ilium, wherein when the fastener is actuated into the first opening, the elongate rod contacts and compresses the tether, thereby securely locking the elongate rod and tether within the clamp, and the tether is securely positioned between a portion vertebral column and the ilium, wherein the anchor is configured to secure the second portion of the tether.

* * * * *